US009468357B2

(12) United States Patent  (10) Patent No.: US 9,468,357 B2
Yanagidate  (45) Date of Patent: Oct. 18, 2016

(54) IMAGE PROCESSING APPARATUS FOR PROCESSING FRAME IMAGE DATA USING DISPLAY CHARACTERISTICS OF THE DESTINATION DISPLAY DEVICE

(71) Applicant: OLYMPUS CORPORATION, Tokyo (JP)

(72) Inventor: Masaharu Yanagidate, Hachioji (JP)

(73) Assignee: OLYMPUS CORPORATION, Tokyo (JP)

(\*) Notice: Subject to any disclaimer, the term of this patent is extended or adjusted under 35 U.S.C. 154(b) by 279 days.

(21) Appl. No.: 14/026,701

(22) Filed: Sep. 13, 2013

(65) Prior Publication Data

US 2014/0015946 A1  Jan. 16, 2014

Related U.S. Application Data

(63) Continuation of application No. PCT/JP2012/055199, filed on Mar. 1, 2012.

(30) Foreign Application Priority Data

Mar. 24, 2011 (JP) .................. 2011-066060

(51) Int. Cl.
*H04N 5/232* (2006.01)
*H04N 5/225* (2006.01)
(Continued)

(52) U.S. Cl.
CPC ............ *A61B 1/00045* (2013.01); *A61B 1/04* (2013.01); *A61B 5/0013* (2013.01);
(Continued)

(58) Field of Classification Search
CPC ... H04N 5/232; H04N 5/225; H04N 5/23229
See application file for complete search history.

(56) References Cited

U.S. PATENT DOCUMENTS 5,805,213 A * 9/1998 Spaulding et al. ......... 348/222.1
6,373,531 B1 * 4/2002 Hidaka et al. ................ 348/603
(Continued)

FOREIGN PATENT DOCUMENTS

CN  1849622  10/2006
CN  101754029  6/2010
(Continued)

OTHER PUBLICATIONS

International Search Report dated Jun. 12, 2012, issued in corresponding application No. PCT/JP2012/055199.
(Continued)

*Primary Examiner* — Abdelaaziz Tissire
(74) *Attorney, Agent, or Firm* — Westerman, Hattori, Daniels & Adrian, LLP (57) ABSTRACT

In an image processing apparatus, a storage circuit stores a parameter of a display processing characteristic in each display device and a parameter of a target value of image quality. The parameter of a target value of image quality includes a parameter of image processing of an image processing circuit to display a predetermined image quality and a parameter of display processing of the display device. An adjustment of image quality in the image processing apparatus is performed by adjusting a processing parameter when performing image processing on the image data that is output to the display device based on the parameter of the display processing characteristic corresponding to the display device that is a destination and on the parameter of the target value of image quality.

5 Claims, 9 Drawing Sheets

(51) Int. Cl.
*A61B 1/00* (2006.01)
*A61B 5/00* (2006.01)
*A61B 1/04* (2006.01)
*H04N 9/73* (2006.01)
*G06F 3/14* (2006.01)
*G09G 3/20* (2006.01)

(52) U.S. Cl.
CPC ......... *A61B 5/7445* (2013.01); *G06F 3/1423* (2013.01); *G09G 3/20* (2013.01); *H04N 5/225* (2013.01); *H04N 5/232* (2013.01); *H04N 5/23229* (2013.01); *H04N 9/73* (2013.01); *A61B 5/0077* (2013.01); *A61B 2560/0437* (2013.01); *G09G 2320/0666* (2013.01); *G09G 2320/0693* (2013.01); *G09G 2340/06* (2013.01); *G09G 2370/10* (2013.01); *G09G 2370/16* (2013.01)

(56) References Cited

U.S. PATENT DOCUMENTS

| | | | |
|---|---|---|---|
| 6,667,765 B1* | 12/2003 | Tanaka | 348/229.1 |
| 2001/0019365 A1* | 9/2001 | Kim et al. | 348/554 |
| 2002/0036645 A1* | 3/2002 | Funahashi | 345/596 |
| 2002/0057374 A1* | 5/2002 | Suzuki | 348/674 |
| 2002/0101514 A1* | 8/2002 | Watanabe | 348/211 |
| 2002/0120781 A1* | 8/2002 | Hirashima et al. | 709/246 |
| 2003/0016289 A1* | 1/2003 | Motomura | H04N 1/46 348/211.5 |
| 2003/0218695 A1* | 11/2003 | Kim et al. | 348/675 |
| 2004/0183915 A1* | 9/2004 | Gotohda et al. | 348/207.11 |
| 2005/0222992 A1* | 10/2005 | Kondo | H04L 12/24 |
| 2007/0097223 A1* | 5/2007 | Ono | 348/211.99 |
| 2007/0165048 A1* | 7/2007 | Yamashita | G06T 5/009 345/601 |
| 2007/0209056 A1* | 9/2007 | Mayuzumi | H04N 1/00127 725/105 |
| 2008/0239157 A1* | 10/2008 | Rai | 348/674 |
| 2009/0015687 A1* | 1/2009 | Shinkai et al. | 348/222.1 |
| 2010/0053441 A1* | 3/2010 | Tokashiki | H04N 5/14 348/576 |
| 2010/0315430 A1* | 12/2010 | Nakashima | G06F 3/1454 345/594 |
| 2013/0057723 A1* | 3/2013 | Mitsugi | 348/222.1 |
| 2013/0342761 A1* | 12/2013 | Wada | H04N 5/38 348/571 |
| 2014/0002625 A1* | 1/2014 | Yanagidate | 348/65 |
| 2014/0169484 A1* | 6/2014 | Jung | H04N 19/172 375/240.29 |

FOREIGN PATENT DOCUMENTS

| | | |
|---|---|---|
| JP | 2003-024273 A | 1/2003 |
| JP | 2003-339634 A | 12/2003 |
| JP | 2004-320614 A | 11/2004 |
| WO | 2006/056616 A1 | 6/2006 |
| WO | 2008/011063 A2 | 1/2008 |

OTHER PUBLICATIONS

Extended European Search Report dated Jan. 29, 2015, issued in corresponding European Patent Application No. 12760639.0 (5 pages).

Office Action dated Jan. 22, 2016, issued in counterpart Chinese Patent Application No. 201280013973.8, with English translation. (17 pages).

* cited by examiner

| USER ID | COLOR GAIN | HUE | GAMMA | FREQUENCY CHARACTERISTIC (0, 0.1, 0.2, 0.3, 0.4, 0.5) | IMAGING DEVICE (ID, GENERATION STATE) | MONITOR ID | MONITOR COLOR TEMPERATURE |
|---|---|---|---|---|---|---|---|
| D001 | 1.1 | 10 | 1.1 | (1, 1, 1, 1.1, 1.2, 1) | (OS01, 0) | DS01 | 6500 |
| D001 | 0.8 | 10 | 0.9 | (1, 1, 1, 1.1, 1.2, 1) | (ES02, 1) | DS01 | 6500 |
| D002 | 1.2 | 350 | 1.4 | (1, 1, 1, 1.2, 1.3, 1) | (ES02, 1) | DS02 | 9300 |
| 0000 | 1.0 | 0 | 0.9 | (1, 1, 1, 1.1, 1.2, 1) | (XR01, 0) | DS01 | 6500 |
| 0000 | 1.0 | 0 | 1.0 | (1, 1, 1, 1, 1, 1) | (0000, 0) | 0000 | 0000 |
| ------ | | ------ | ------ | ------ | ------ | ------ | |

FIG. 7

| ID | COLOR GAIN | HUE | GAMMA | FREQUENCY CHARACTERISTIC (0, 0.1, 0.2, 0.3, 0.4, 0.5) | COLOR TEMPERATURE |
|---|---|---|---|---|---|
| DS01 | 0.8 | 0 | 2.2 | (1, 1, 1, 1.2, 1.2, 1) | 6500 |
| DS02 | 0.9 | 0 | 1.8 | (1, 1, 1, 1, 1.2, 1) | 9300 |

IMAGE PROCESSING APPARATUS FOR PROCESSING FRAME IMAGE DATA USING DISPLAY CHARACTERISTICS OF THE DESTINATION DISPLAY DEVICE

CROSS-REFERENCE TO RELATED APPLICATION

This is Continuation Application of International Patent Application No. PCT/JP2012/055199 filed Mar. 1, 2012, which claims priority to Japanese Patent Application No. 2011-066060, filed Mar. 24, 2011. The contents of the aforementioned application are incorporated herein by reference.

BACKGROUND OF THE INVENTION

1. Field of the Invention

The present invention relates to an image-processing apparatus that performs image processing on frame image data that is input from an imaging device.

2. Description of Related Art

When a display device displays a captured image generated by an imaging device, image processing is performed on the captured image and image data for display suitable for the characteristics of the display device is generated. For example, in Japanese Unexamined Patent Application, First Publication No. 2004-320614, a parameter of the display device is acquired from the exterior and image processing corresponding to the parameter is performed on an image signal. Japanese Unexamined Patent Application, First Publication No. 2004-320614 discloses a method for generating an image signal for display.

However, in the method disclosed in Japanese Unexamined Patent Application, First Publication No. 2004-320614, it is not possible to display an image corresponding to the favorites of a user who uses the display device.

SUMMARY OF THE INVENTION

An image-processing apparatus according to a first aspect of the present invention includes at communication unit, an image processing unit, an output unit, a storage unit, and an adjustment unit. The communication unit receives frame image data from an imaging device that images an object and transmits the frame image data. The image processing unit performs image processing on the frame image data that is received by the communication unit. The output unit outputs the frame image data having been image-processed by the image processing unit to a display device that displays the frame image data. The storage unit stores a parameter of target value of image quality based on a characteristic obtained by combining an image processing characteristic of the image processing unit with the display processing characteristic of the display device, and a parameter of the display processing characteristic of the display device. The image processing unit includes an adjustment unit which adjusts a processing parameter when the image processing unit performs the image processing on the frame image data that is output to the display device based on the parameter of the display processing characteristic stored in the storage unit and corresponding to the display device that is a destination of the frame image data, and on the parameter of target value of image quality stored in the storage unit.

Furthermore, according to a second aspect of the present invention, in the image processing apparatus of the first aspect, the storage unit further stores a parameter of the imaging characteristic of the imaging device. The adjustment unit adjusts the processing parameter when the image processing unit performs the image processing on the frame image data that is output to the display device based on the parameter of the display processing characteristic stored in the storage unit and corresponding to the display device that is a destination of the frame image data, on the parameter of the target value of image quality, and on the parameter of the imaging characteristic corresponding to the imaging device transmitting the frame image data to the image processing apparatus.

Furthermore, according to a third aspect of the present invention, in the image processing apparatus of the first aspect, a user interface unit allows users to set the parameter of the target value of image quality. The parameter of the target value of the image quality is managed with respect to each of the users using an identifier being given to at last each of the users.

Furthermore, according to a fourth aspect of the present invention, in the image processing apparatus of the first aspect, the communication unit transmits the parameter of the target value of image quality stored in the storage unit to another image processing apparatus, or receives the parameter of the target value of image quality from another image processing apparatus.

Furthermore, according to a fifth aspect of the present invention, in the image processing apparatus of the first aspect, when the communication unit receives the parameter of the target value of image quality from another image processing apparatus, the adjustment unit adjusts the processing parameter which is used when the image processing unit performs the image processing on the frame image data that is output to the display device based on the parameter of the target value of image quality received by the communication unit.

DETAILED DESCRIPTION OF THE INVENTION

Hereinafter, with reference to the accompanying drawings, embodiments of the present invention will be described. Hereinafter, a description will be provided for the case in which embodiments of the present invention are applied to an imaging display system including a medical imaging device, a transmission device, a reception device, and a display monitor.

(First Embodiment)

Figure 1:
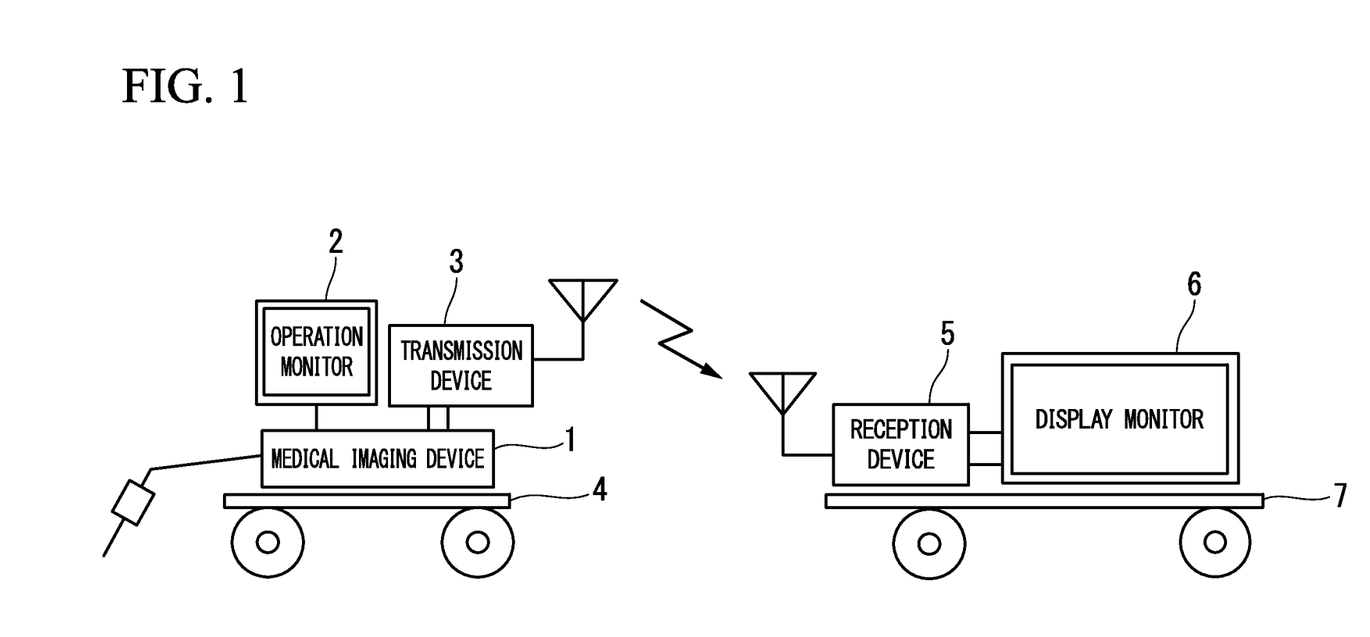
FIG. 1 is a block diagram illustrating a constitution of an imaging display system according to a first embodiment of the present invention.

A first embodiment according to the present invention will be described. FIG. 1 illustrates a constitution of an imaging display system according to the present embodiment. In FIG. 1, a medical imaging device 1, an operation monitor 2 that displays a captured image generated by the medical imaging device 1 or various control screens, and a transmission device 3 that performs wireless transmission of image data are mounted on a cart 4. A reception device 5 that receives the image data transmitted from the transmission device 3 and outputs a video signal, and a display monitor 6 that displays the video signal output from the reception device 5 as an image are mounted on a cart 7.

The medical imaging device 1 continuously generates image data of each frame (frame image data) of moving image data including a plurality of frames. The image data generated by the medical imaging device 1 is wirelessly transmitted from the transmission device 3 to the reception device 5, and an image is displayed on the display monitor 6 connected to the reception device 5. The transmission device 3 packetizes the image data output from the medical imaging device 1 and wirelessly transmits a packet. Furthermore, the reception device 5 performs image processing on the image data extracted from the received packet to generate a video signal, and outputs the video signal to the display monitor 6. The display monitor 6 performs display processing on the video signal and displays an image.

Figure 2:
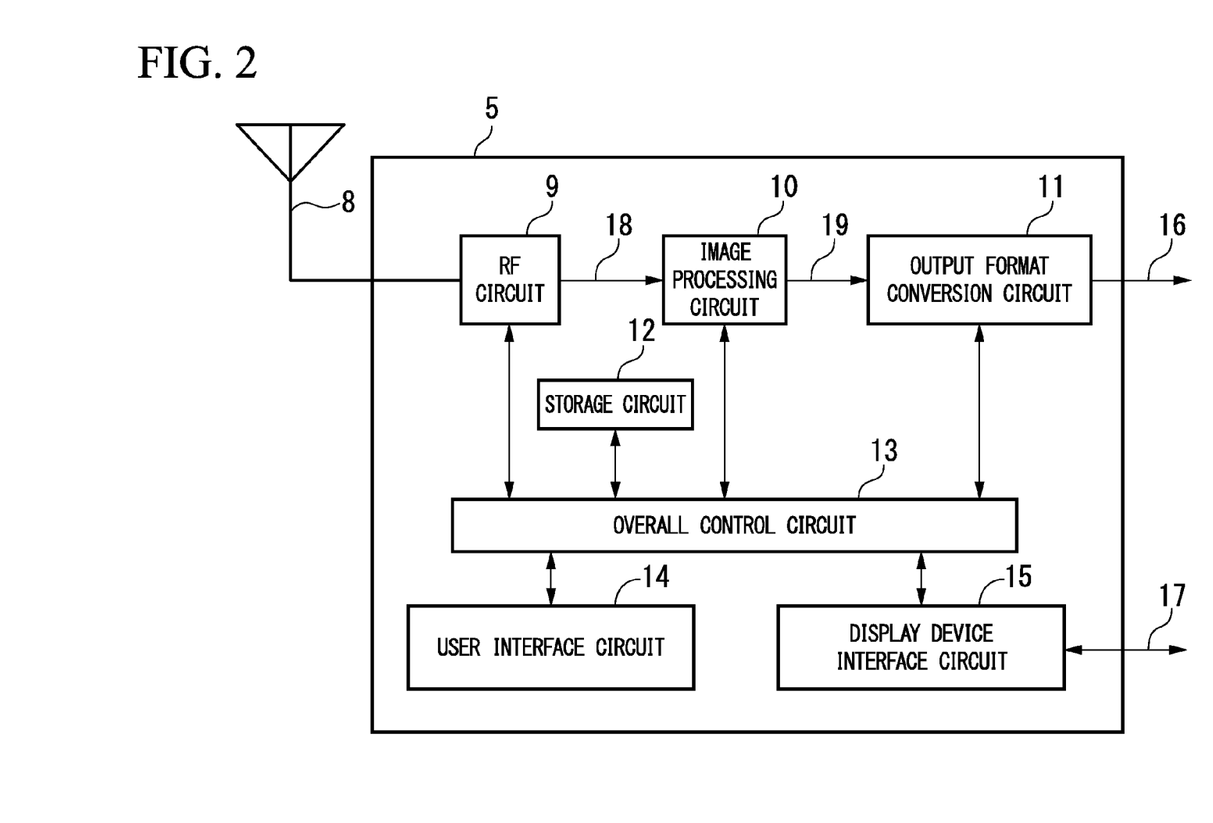
FIG. 2 is a block diagram illustrating a constitution of a reception device provided in an imaging display system according to the first embodiment of the present invention.

FIG. 2 illustrates a constitution of the reception device 5. The reception device 5 includes an antenna 8, an RF circuit 9, an image processing circuit 10, an output format conversion circuit 11, a storage circuit 12, an overall control circuit 13, a user interface circuit 14, and a display device interface circuit 15.

The antenna 8 receives, as a wireless signal, the image data wirelessly transmitted from the transmission device 3. The RF circuit 9 performs high frequency processing of the received wireless signal, and outputs image data 18 including Y (luminance), U (a color difference Cb), and V (a color difference Cr) to the image processing circuit 10. The image processing circuit 10 performs image processing on the image data 18 by a method which will be described later, and outputs adjusted image data 19, which has image quality adjusted to be desired image quality, to the output format conversion circuit 11. The output format conversion circuit 11 converts a format of the adjusted image data 19 to an output format suitable for an image input interface of the display monitor 6, and outputs a video signal 16 to the display monitor 6.

The overall control circuit 13 is a circuit that controls an entire operation of the reception device 5. The storage circuit 12 is a circuit that stores image quality adjustment target information which will be described later, and parameters necessary for various types of processing. The user interface circuit 14 is a circuit that receives instruction content instructed by a user and transfers the instruction content to the overall control circuit 13. The instruction content is interpreted by the overall control circuit 13 and is stored in the storage circuit 12 according to necessity. The display device interface circuit 15 is connected to the display monitor 6. The display device interface circuit 15 acquires parameter values of display process characteristics from the display monitor 6, and stores the parameter values in the storage circuit 12 through the overall control circuit 13.

Figure 3:
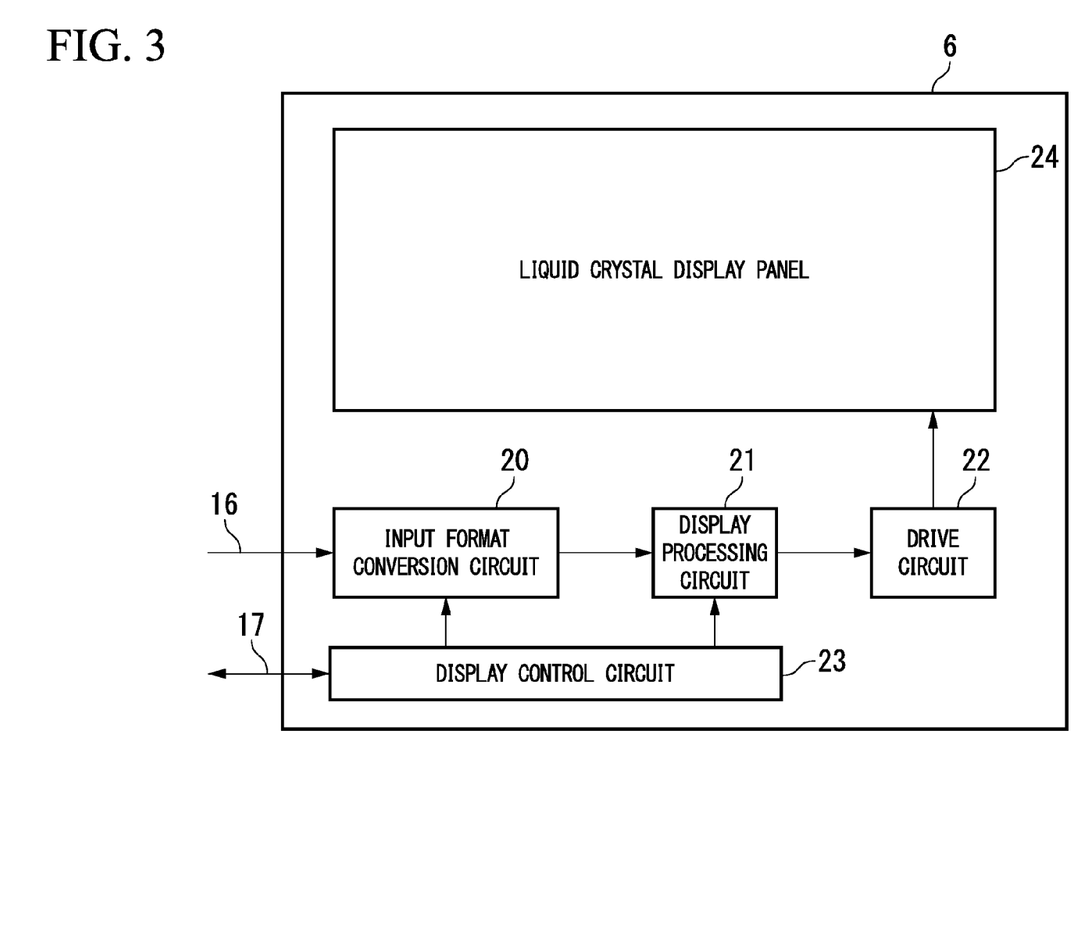
FIG. 3 is a block diagram illustrating a constitution of a display monitor provided in an imaging display system according to the first embodiment of the present invention.

FIG. 3 illustrates a constitution of the display monitor 6. The display monitor 6 includes an input format conversion circuit 20, a display processing circuit 21, a drive circuit 22, a display control circuit 23, and a liquid crystal display panel 24. The input format conversion circuit 20 converts a format of the video signal 16 output from the reception device 5, restores image data including Y (luminance), U (a color difference Cb), and V (a color difference Cr), and outputs the image data to the display processing circuit 21. The display processing circuit 21 performs image quality adjustment on the image data processed in the input format conversion circuit 20, and outputs the processed image data to the drive circuit 22. The drive circuit 22 drives the liquid crystal display panel 24 such that an image based on the image data processed in the display processing circuit 21 is displayed. The liquid crystal display panel 24 displays an image captured in the medical imaging device 1.

The display control circuit 23 is a circuit that controls an entire operation of the display monitor 6. The display control circuit 23 notifies the reception device 5 of parameter values of display processing characteristics including display characteristics of the liquid crystal display panel 24 and processing characteristics of the display processing circuit 21 via a display device interface signal 17, for example, when the system operation is started. When the display device interface signal 17 including parameter values (including an ID of the display monitor 6) of display processing characteristics of the display monitor 6 are input to the display device interface circuit 15, the overall control circuit 13 in the reception device 5 stores the parameter values of the display processing characteristics of the display monitor 6 in the storage circuit 12.

Figure 4:
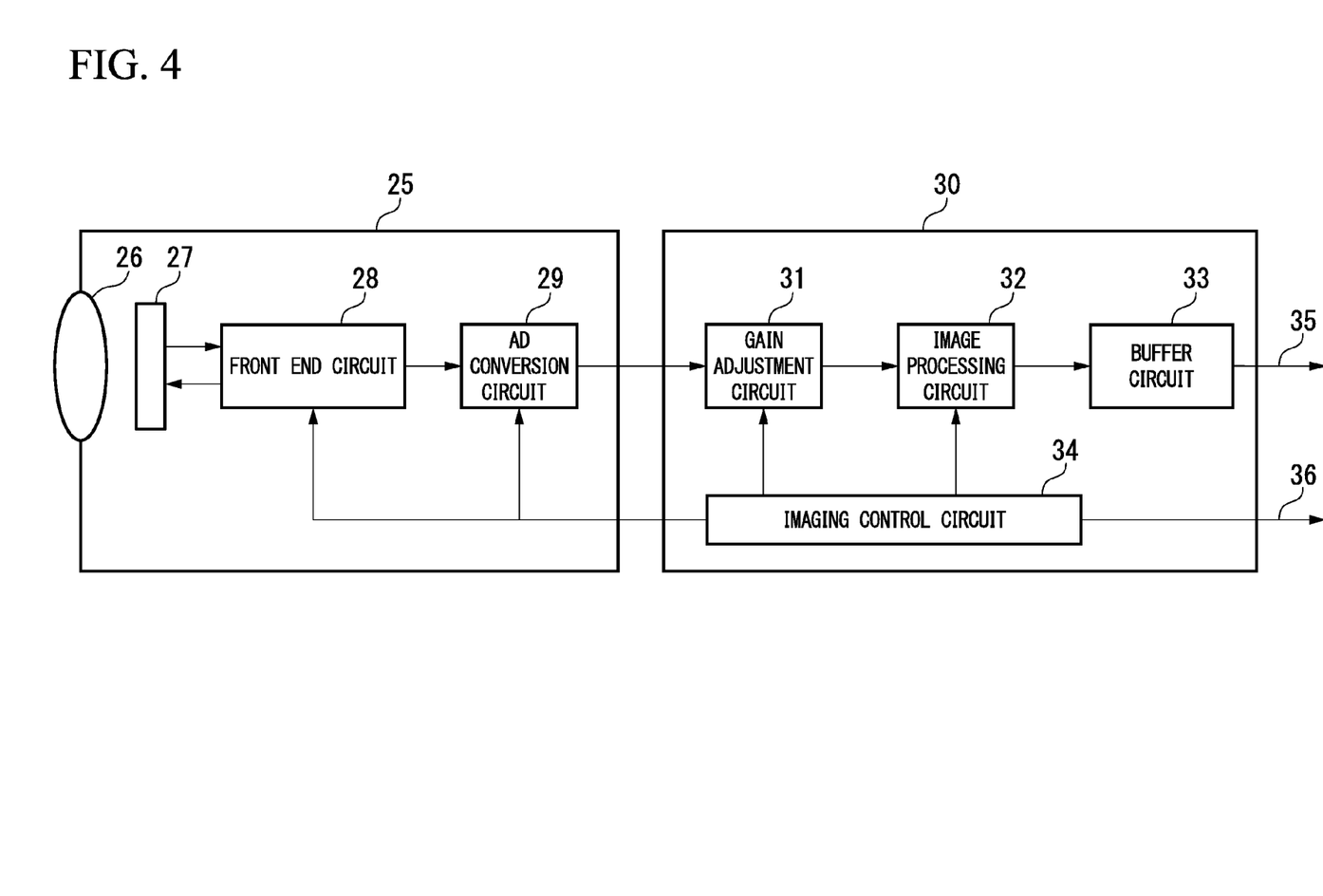
FIG. 4 is a block diagram illustrating a constitution of a medical imaging device provided in an imaging display system according to the first embodiment of the present invention.

FIG. 4 illustrates a constitution of the medical imaging device 1. The medical imaging device 1 includes a camera head 25 and a camera control unit 30. The camera head 25 includes an imaging optical system 26, an imaging element 27, a front end circuit 28, and an AD conversion circuit 29. The camera control unit 30 includes a gain adjustment circuit 31, an image processing circuit 32, a buffer circuit 33, and an imaging control circuit 34.

The imaging optical system 26 allows an object image incident from an exterior to be formed on the imaging element 27. The imaging element 27 images the object image formed by the imaging optical system 26, and generates an imaging signal. The front end circuit 28 drives the imaging element 27, performs signal processing on the imaging signal output from the imaging element 27, and outputs an analog imaging signal to the AD conversion circuit 29. The AD conversion circuit 29 converts the analog imaging signal processed in the front end circuit 28 into digital data, and outputs the digital data to the camera control unit 30. Since the operation content of the camera head 25 is well known in the related art, a detailed description thereof will be omitted.

The gain adjustment circuit 31 performs gain control processing on the digital data output from the camera head 25, and outputs the processed digital data to the image processing circuit 32. The image processing circuit 32 performs image quality adjustment processing on the digital data processed in the gain adjustment circuit 31, and outputs the processed digital data to the buffer circuit 33. The buffer circuit 33 performs output impedance conversion on the digital data processed in the image processing circuit 32, and outputs image data 35 to the transmission device 3. Since image quality adjustment and RGB-YC conversion are performed in the image processing circuit 32, the image data 35 including a YUV signal is output from the camera control unit 30.

The imaging control circuit 34 is a circuit that controls the camera head 25 and the camera control unit 30. The imaging control circuit 34 notifies the transmission device 3 of parameter values of imaging characteristics, which are obtained by integrating characteristics of the imaging element 27 and characteristics of the image quality adjustment processing by the image processing circuit 32, via an imaging device interface signal 36, for example, when the system operation is started. The transmission device 3 notified of the parameter values of the imaging characteristics by the medical imaging device 1 transmits a packet including the parameter values (including an ID of the medical imaging device 1) of the imaging characteristics to the reception device 5. When the packet is received by the reception device 5, the overall control circuit 13 acquires the parameter values of the imaging characteristics from the RF circuit 9, and stores the acquired parameter values in the storage circuit 12.

Figure 5:
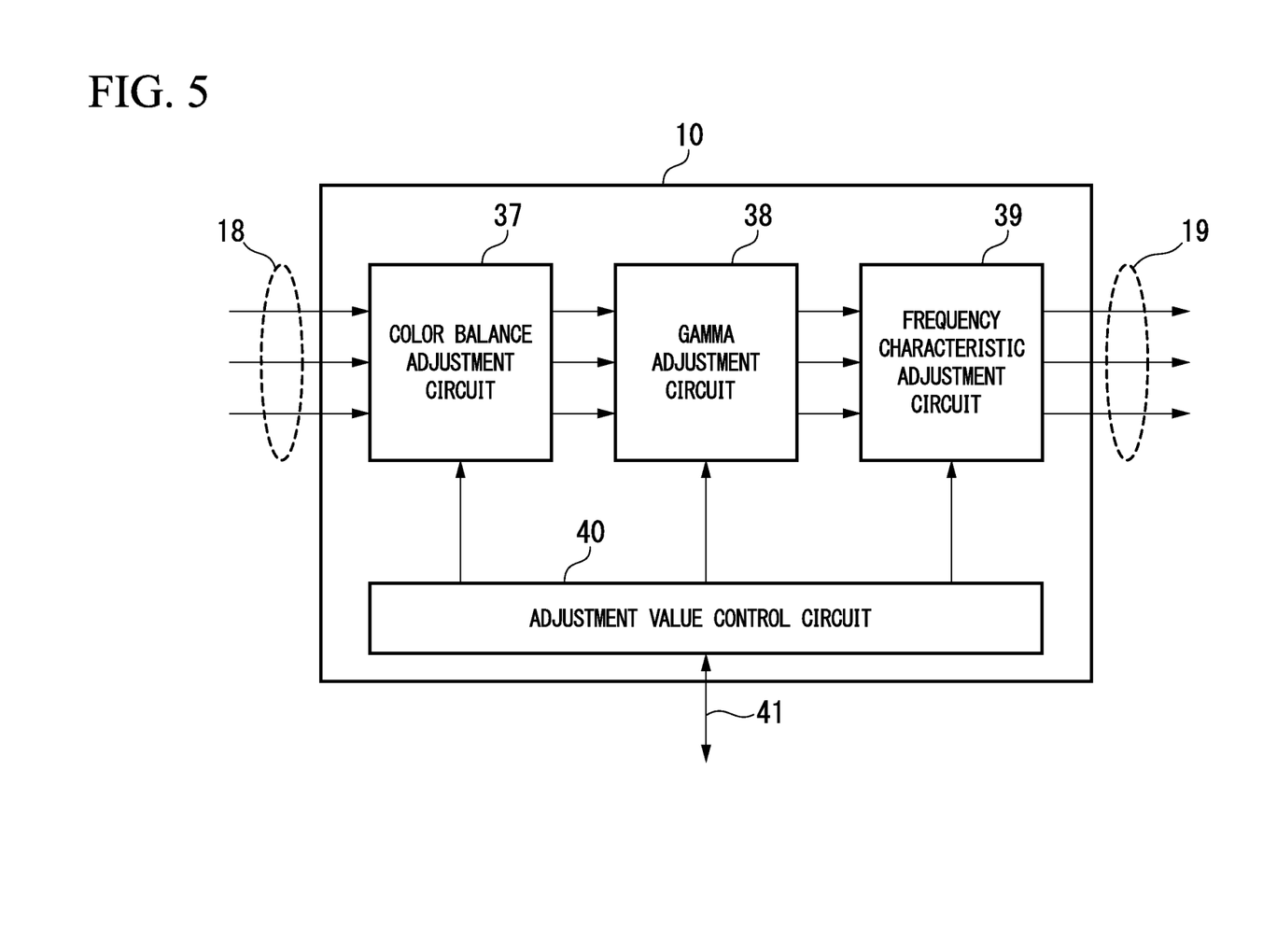
FIG. 5 is a block diagram illustrating a constitution of an image processing circuit of a reception device provided in an imaging display system according to the first embodiment of the present invention.

FIG. 5 illustrates a constitution of the image processing circuit 10 of the reception device 5. The image processing circuit 10 includes a color balance adjustment circuit 37, a gamma adjustment circuit 38, a frequency characteristic adjustment circuit 39, and an adjustment value control circuit 40. The color balance adjustment circuit 37 adjusts a color gain and hue of the image data 18, which is output from the RF circuit 9 and includes Y (luminance), U (a color difference Cb), and V (a color difference Cr), and outputs the processed image data to the gamma adjustment circuit 38. The gamma adjustment circuit 38 performs gamma adjustment on the image data processed in the color balance adjustment circuit 37, and outputs the processed image data to the frequency characteristic adjustment circuit 39. The frequency characteristic adjustment circuit 39 performs frequency adjustment on the image data processed in the gamma adjustment circuit 38, and outputs the adjusted image data 19. The adjustment value control circuit 40 is a circuit that controls the image processing circuit 10 based on an instruction given from the overall control circuit 13 through a control signal 41. Details of the color gain and hue adjustment, the gamma adjustment, and the frequency adjustment will be described later.

Figure 6:
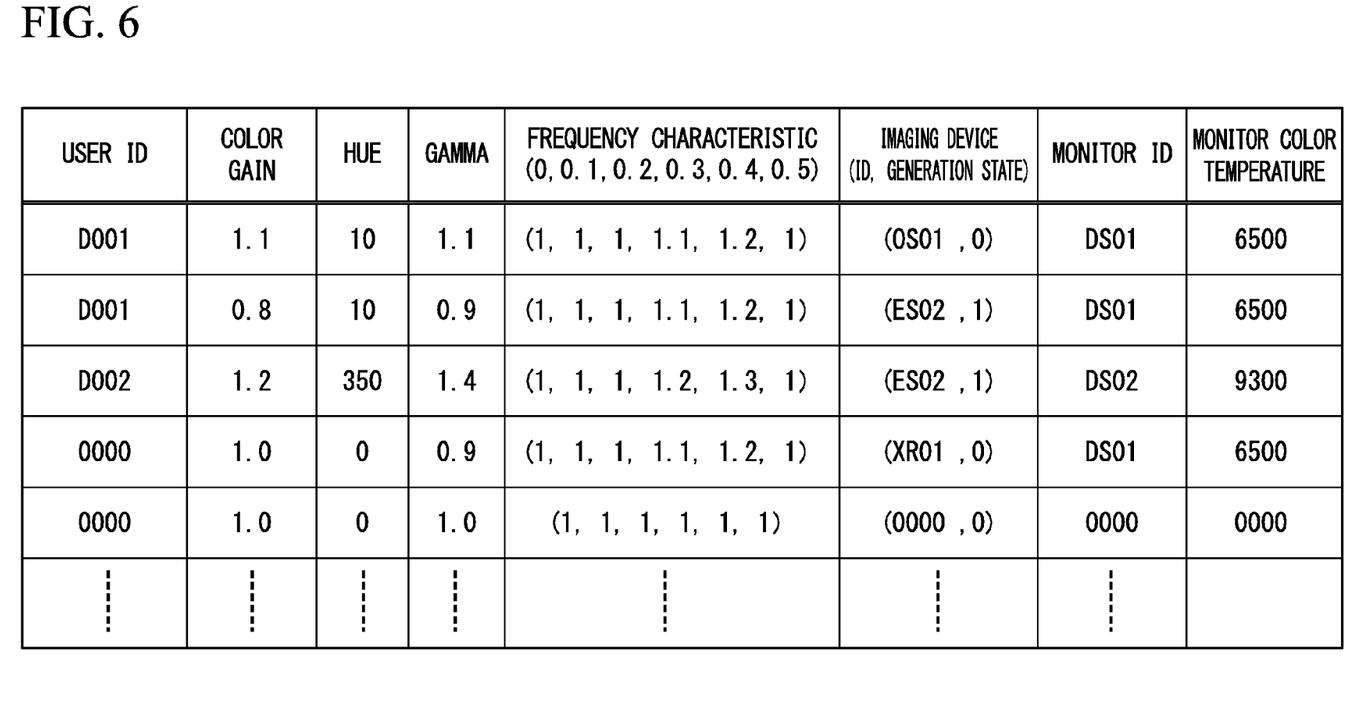
FIG. 6 is a reference diagram illustrating image quality adjustment target information in the first embodiment of the present invention.

FIG. 6 is an example of image quality adjustment target information used in the image quality adjustment performed by the reception device 5. The image quality adjustment target information of the present embodiment is target values of parameters (the color gain, the hue, the gamma, and the frequency characteristic in FIG. 6) corresponding to the image quality of an image displayed on the display monitor 6, which is required by a user. Furthermore, the image quality adjustment target information is based on characteristics obtained by matching the characteristics of the image quality adjustment (the image processing) performed by the image processing circuit 10 of the reception device 5 with the characteristics of the display processing by the display monitor 6. In addition, the image quality adjustment target information is also based on the imaging characteristics of the medical imaging device 1. As described above, the image quality adjustment target information is based on the characteristics of the image quality adjustment performed by the image processing circuit 10, the characteristics of the display processing by the display monitor 6, and the imaging characteristics of the medical imaging device 1. However, the image quality adjustment target information is not information that individually designates the respective characteristics, but indicates characteristics of image quality finally obtained by integrating the respective characteristics. The image quality adjustment is performed by the image processing circuit 10 of the reception device 5 such that parameters of image quality after the image quality adjustment performed by the image processing circuit 10 of the reception device 5 and the display processing by the display monitor 6 are performed are each value of the image quality adjustment target information as illustrated in FIG. 6.

As illustrated in FIG. 6, the image quality adjustment target information includes a user ID, a color gain, hue, gamma, a frequency characteristic, a generation state flag, and a monitor color temperature. The user ID is an identifier for identifying users who have generated the image quality adjustment target information. The color gain and the hue (0° to 360°) are target values of chroma and hue of a display image. The gamma is a target value of gamma adjustment of the display image. The frequency characteristic is a target value of a frequency characteristic of the display image. Furthermore, the frequency characteristic is normalized for display by setting a sampling frequency to 1, and is defined with a gain at each frequency of 0, 0.1, 0.2, 0.3, 0.4, and 0.5 commonly in both the horizontal direction H and the vertical direction V. The generation state flag includes an ID of an imaging device used for generating the image quality adjustment target information, and a flag (0: not included and 1: included) indicating whether the image quality adjustment target information is image quality adjustment target information including imaging characteristics. The monitor color temperature includes the ID of the display monitor 6 used for generating the image quality adjustment target information, and a monitor color temperature that is color temperature setting at the time of generation thereof.

Figure 7:
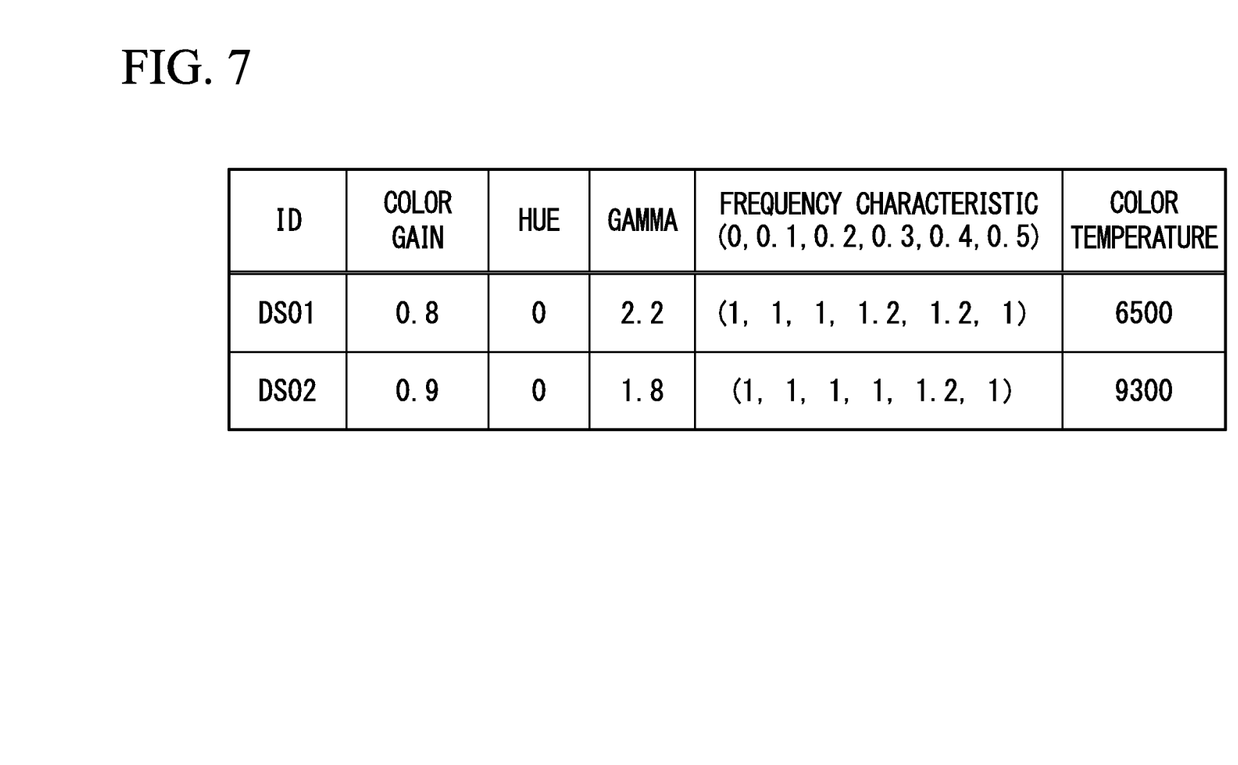
FIG. 7 is a reference diagram illustrating image quality characteristics in the first embodiment of the present invention.

FIG. 7 is an example of the display characteristics including the parameters of the display processing characteristics of the display monitor 6. The display monitor 6 performs display processing using the parameters illustrated in FIG. 7. As illustrated in FIG. 7, the display characteristics of the display monitor 6 include an ID, a color gain, hue, gamma, a frequency characteristic, and a color temperature. The ID is an identifier for identifying the display monitor 6. The color gain and the hue are adjustment values of a chroma component and hue based on the display processing performed in the display processing circuit 21 of the display monitor 6. The gamma is obtained by matching the display characteristics of the liquid crystal display panel 24 with the characteristics of the display processing performed in the display processing circuit 21. The frequency characteristic is a characteristic of contour correction processing performed in the display processing circuit 21. The color temperature is color temperature setting at the time of generation of the image quality adjustment target information.

Figure 8:
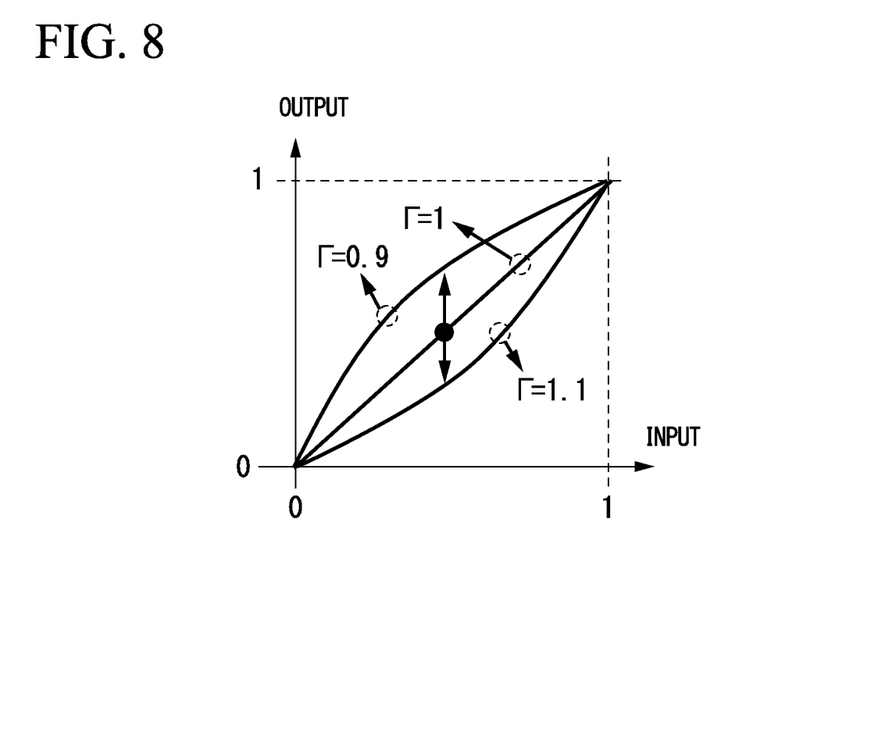
FIG. 8 is a reference diagram illustrating gamma in the first embodiment of the present invention.

FIG. 8 is a characteristic example of the gamma of the image quality adjustment target information. In a normal display monitor, the gamma of the device is set to 2.2 or 1.8. The imaging device offsets the gamma of the display monitor in the state in which the imaging device and the display monitor have been connected to each other, and performs inverse correction (1/Γ correction) such that the gamma is 1.

FIG. 8 illustrates the degree by which the gamma deviates from (gamma=1) in response to the favorites of a user. Input/output characteristics in three cases in which the gamma is 0.9, the gamma is 1, and the gamma is 1.1 in the image quality adjustment target information are illustrated in FIG. 8.

Figure 9:
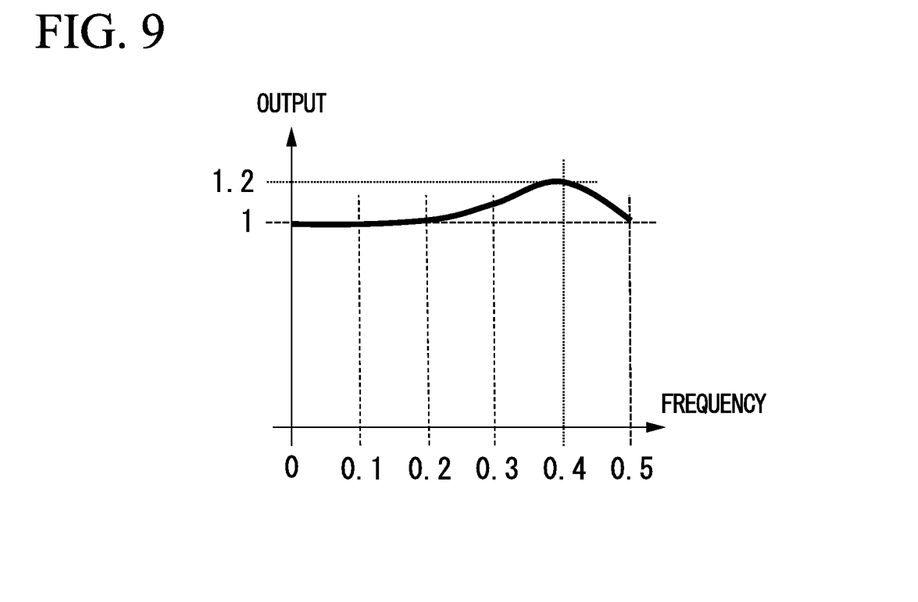
FIG. 9 is a reference diagram illustrating frequency characteristics in the first embodiment of the present invention.

FIG. 9 is an example of the frequency characteristic of the image quality adjustment target information. The frequency characteristic in the present example is a target value related to adjustment of a frequency characteristic in the case of a user having a user ID of D001 as illustrated in FIG. 6. In the frequency characteristic illustrated in FIG. 9, a gain of a high frequency component is jumped. Therefore, when the frequency characteristic illustrated in FIG. 9 is set as a target value, an image displayed on the display monitor is an image in which a contour part having many high frequency components has been emphasized.

Next, using FIG. 6 and FIG. 7, a description of a generation method of image quality adjustment target information and an image quality adjustment method by the image processing circuit 10 using the image quality adjustment target information will be provided. First, a description of a generation method of image quality adjustment target information in the case of using an imaging device that does not output information indicating imaging characteristics will be provided.

At the time of generation of the image quality adjustment target information, in the state in which an image captured by the medical imaging device 1 has been displayed on the display monitor 6, an adjustment value, which is a parameter indicating the characteristics of image quality adjustment (image processing) performed by the image processing circuit 10 of the reception device 5, is adjusted according to the instruction content of a user. As described above, the instruction content of the user is input to the overall control circuit 13 through the user interface circuit 14, and the adjustment value control circuit 40 of the image processing circuit 10 is notified of the instruction content as the control signal 41 by the overall control circuit 13.

The adjustment value control circuit 40 adjusts the adjustment value of the image processing circuit 10 in response to the instruction content of the user, which has been notified via the control signal 41. When the image quality of an image displayed on the display monitor 6 is a user's favorite image quality, information indicating that the image quality of the image is the user's favorite image quality is input to the overall control circuit 13 through the user interface circuit 14. Moreover, the adjustment value control circuit 40 is notified of the information indicating that the image quality of the image is the user's favorite image quality via the control signal 41. The adjustment value control circuit 40 generates image quality adjustment target information using an adjustment value at this time, and notifies the overall control circuit 13 of the image quality adjustment target information via the control signal 41. The overall control circuit 13 stores the image quality adjustment target information notified from the adjustment value control circuit 40 in the storage circuit 12.

In the case of using the imaging device that does not output the information indicating imaging characteristics, since the imaging characteristics of the imaging device are not known, the overall control circuit 13 generates the image quality adjustment target information on the assumption that the imaging characteristics are standard characteristics. In the present description, the standard characteristics are set as inverse characteristics when the color gain is 1.0, the hue is 0°, the gamma is monitor γ: 2.2, and the frequency characteristic is flat (no contour emphasis). Furthermore, the display characteristics of the display monitor (ID=DS01) are values illustrated in FIG. 7. When the adjustment value of the image quality adjustment of the image processing circuit 10 at the time at which the image quality of an image displayed on the display monitor 6 is the user's favorite image quality, for example, the color gain is 1.375, the hue is 10°, the gamma is 1.1, and the frequency characteristic is (1, 1, 1, 0.92, 1, and 1) [a gain at a frequency/a sampling frequency is (0, 0.1, 0.2, 0.3, 0.4, and 0.5)], the image quality adjustment target information is generated as follows.

For the color gain, since the standard characteristic is 1.0, the display characteristic is 0.8, and the adjustment value is 1.375, a target value of the color gain is 1.1(=1*0.8*1.375). For the hue, since the standard characteristic is 0, the display characteristic is 0, and the adjustment value is 10, a target value of the hue is 10(=0+0+10). For the gamma, since the standard characteristic is [an inverse characteristic when γ is set to 2.2], the display characteristic is 2.2, and the adjustment value is 1.1, a target value of the gamma is 1.1. For the frequency characteristic, since the standard characteristic is (1, 1, 1, 1, 1, and 1), the display characteristic is (1, 1, 1, 1.2, 1.2, and 1), and the adjustment value is (1, 1, 1, 0.92, 1, and 1), a target value of the frequency characteristic is (1, 1, 1, 1.1, 1.2, and 1). For example, at a frequency of 0.4, since the standard characteristic is 1, the display characteristic is 1.2, and the adjustment value is 0.92, a target value is 1.1 (=1*1.2*0.92).

The image quality adjustment target information is generated by the above procedure. The generated image quality adjustment target information is written in the storage circuit 12 as illustrated in FIG. 6 in the state of clearly specifying that the generation state flag is set to 0 and no imaging characteristics are included.

Next, the image quality adjustment method will be described. Hereinafter, a description will be provided for image quality adjustment using the image quality adjustment target information obtained by the above procedure when a display monitor (ID=DS02)) having display characteristics different from those of a display monitor (ID=DS01) has been connected.

As illustrated in FIG. 7, the color temperature of the display monitor (ID=DS01) is 6500 K and the color temperature of the display monitor (ID=DS02)) is 9300 K. When the color temperatures differ from each other, a color tone when a signal value of an image is saturated (white) differs in each display monitor. Since it is difficult to completely adjust the color temperature through the image processing in the reception device 5, the color temperature of the display monitor 6 is changed from the reception device 5 in the present embodiment. The setting of the color temperature of the display device, in which image quality adjustment is not sufficient through only the image processing, is performed based on an instruction from the reception device 5, resulting in the improvement of the adjustment accuracy of display image quality.

Accordingly, the overall control circuit 13 of the reception device 5 generates change information for changing the color temperature of the display monitor 6, and outputs the change information to the display monitor 6 from the display device interface circuit 15 via the display device interface signal 17. The display control circuit 23 of the display monitor 6 changes its own color temperature based on the change information notified via the display device interface signal 17. In this case, since the image quality adjustment target information is generated in the state in which the display monitor (ID=DS1) having the color temperature of 6500 K has been connected, after the color temperature of the display monitor (ID=DS02)) in the image quality adjustment target information is changed to 6500 K, the image quality adjustment is performed.

The display characteristics of the display monitor (ID=DS02)) are assumed to be the values illustrated in FIG. 7. As described above, in relation to the image quality adjustment target information, since the color gain is 1.1, the hue is 10°, the gamma is 1.1, and the frequency characteristic is (1, 1, 1, 1.1, 1.2, and 1), the adjustment value of the image processing circuit 10 is as follows. For the color gain, since the standard characteristic is 1.0, the display characteristic is 0.9, and the image quality adjustment target is 1.1, an adjustment value of the color gain is 1.222(=1*1.1/0.9). For the hue, since the standard characteristic is 0, the display characteristic is 0, and the image quality adjustment target is 10, an adjustment value of the hue is 10(=0+0+10).

For the gamma, since the standard characteristic is [an inverse characteristic when γ is set to 2.2], the display characteristic is 1.8, and the image quality adjustment target is 1.1, an adjustment value of the gamma is a characteristic obtained by adding γ(=1.1) to a result obtained by subtracting an inverse characteristic when γ is set to 1.8 from the inverse characteristic when γ is set to 2.2. The gamma adjustment circuit 38 of the image processing circuit 10 includes a look-up table and the adjustment value control circuit 40 calculates the adjustment value of the gamma and writes it in the table, so that it is also possible to perform processing requiring complicated calculation.

For the frequency characteristic, since the standard characteristic is (1, 1, 1, 1, 1, and 1), the display characteristic is (1, 1, 1, 1, 1.2, and 1), and the image quality adjustment target is (1, 1, 1, 1.2, 1, and 1), an adjustment value is (1, 1, 1, 1, 1, and 1). Since the image quality adjustment is performed using the adjustment values, even when the display monitor (ID=DS02)) having different display characteristics is connected, it is possible to display an image with desired image quality.

At the time of the image quality adjustment, the overall control circuit 13 reads information on the image quality adjustment target, the display characteristics of the display monitor (ID=DS02)), and the imaging characteristics (the standard characteristics in the above example) from the storage circuit 12, and outputs the information to the image processing circuit 10. The adjustment value control circuit 40 of the image processing circuit 10 calculates each adjustment value as above based on the information, and controls the color balance adjustment circuit 37, the gamma adjustment circuit 38, and the frequency characteristic adjustment circuit 39 based on the calculated adjustment values.

Next, a description of a generation method of image quality adjustment target information in the case of using an imaging device that outputs the information indicating imaging characteristics will be provided. The information indicating imaging characteristics is wirelessly transmitted from the imaging control circuit 34 of the medical imaging device 1 to the reception device 5 through the transmission device 3, and is stored in the storage circuit 12 of the reception device 5. The subsequent processing is performed by replacing information, which has been used as standard characteristics in a description about the generation method of the image quality adjustment target information in the case of using the imaging device that does not output the information indicating imaging characteristics, with the information indicating imaging characteristics. Since the same processing is performed except for this, a detailed description will be omitted.

As described above, according to the present embodiment, the adjustment value of the image quality adjustment in the image processing circuit 10 is decided using image quality adjustment target information corresponding to desired image quality and display characteristics of each display monitor. Thereby, it is possible to offset a difference of the display characteristics by adjusting image processing characteristics, even in the case of using the display monitor 6 having different display characteristics. Consequently, it is possible to adjust the image quality of an image displayed on the display monitor 6 to desired image quality.

Furthermore, the adjustment value of the image quality adjustment in the image processing circuit 10 is decided using image quality adjustment target information corresponding to desired image quality, display characteristics of each display monitor, and imaging characteristics of each imaging device, so that it is possible to offset a difference of the imaging characteristics by adjusting image processing characteristics, even in the case of using the medical imaging device 1 having different imaging characteristics. Consequently, it is possible to adjust the image quality of an image displayed on the display monitor 6 to desired image quality.

Furthermore, at the time of generation of image quality adjustment target information, a user is able to perform adjustment while confirming the image quality of an image that is displayed. That is, it is possible to manage the image quality adjustment target information for each user. Consequently, it is possible to display an image with image quality corresponding to the favorites of each user. Moreover, the image quality adjustment target information is generated for each user, so that it is possible to perform image quality adjustment corresponding to the favorites of each user.

(Second Embodiment)

Figure 10:
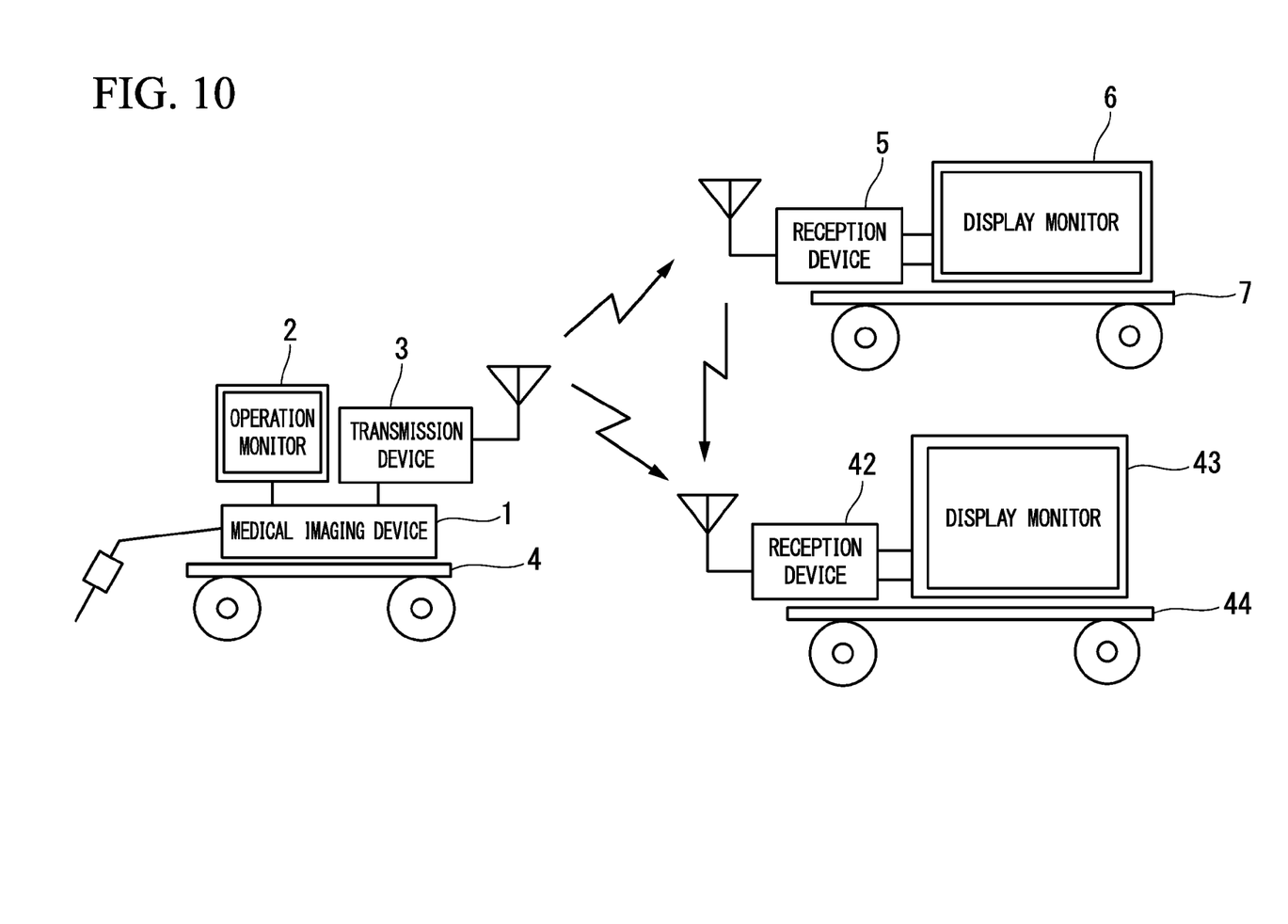
FIG. 10 is a block diagram illustrating a constitution of an imaging display system according to a second embodiment of the present invention.

Next, a second embodiment of the present invention will be described. FIG. 10 illustrates a constitution of an imaging display system according to the present embodiment. In FIG. 10, a medical imaging device 1, an operation monitor 2, and a transmission device 3 are mounted on a cart 4. A reception device 5 and a display monitor 6 are mounted on a cart 7. A reception device 42 and a display monitor 43 are mounted on a cart 44. In the second embodiment, display characteristics of the two display monitors (the display monitor 6 and the display monitor 43) differ from each other.

A characteristic operation in the present embodiment is an image quality correlation operation for allowing the image quality of images displayed on the two display monitors 6 and 43 to be equal to each other. In the image quality correlation operation of the present embodiment, the reception device 5 is set as a main reception device and the reception device 42 is set as a sub-reception device. The main reception device 5 transmits image quality adjustment target information to the sub-reception device 42, so that the main reception device 5 and the sub-reception device 42 perform image quality adjustment using the same image quality adjustment target information. In this way, the image quality of images displayed on the two display monitors 6 and 43 is adjusted to image quality corresponding to the same image quality adjustment target information.

When performing the above operations, the overall control circuit 13 of the reception device 5 reads the image quality adjustment target information shared by the reception device 42 from the storage circuit 12, and transmits a packet including the image quality adjustment target information to the reception device 42 through the RF circuit 9 and the antenna 8. The reception device 42 has the same constitution as that of FIG. 2, and stores the image quality adjustment target information included in the packet received from the reception device 5 in its own storage circuit. Since details of an image quality adjustment operation in the reception device 42 are the same as in the operation described in the first embodiment, a description thereof will be omitted.

As described above, according to the present embodiment, it is possible to match the image quality of an image displayed on the display monitor 6 connected to the main reception device 5 with the image quality of an image displayed on the display monitor 43 connected to the sub-reception device 42. Consequently, it is possible to adjust display image quality of a plurality of display devices in the imaging display system.

While preferred embodiments of the invention have been described and illustrated above, it should be understood that detailed constitutions are not limited to the embodiments. Design modifications can be made without departing from the spirit or scope of the present invention.

What is claimed is:

1. An image processing apparatus comprising:
   a communication circuit receiving frame image data generated by an imaging device;
   an image processing circuit performing image processing on the frame image data that is received by the communication circuit;
   an output circuit outputting the frame image data processed by the image processing circuit to a display device that displays an image based on the processed frame image data; and,
   a storage circuit storing a parameter of target value of image quality of the image to be displayed on the display device according to a requirement by a user, and a parameter of the display processing characteristic of the display device connected to the image processing apparatus,
   wherein the image processing circuit includes an adjustment control circuit which determines a processing parameter when the image processing circuit performs the image processing on the frame image data by using the parameter of the display processing characteristic corresponding to the currently connected display device that is a destination of the frame image data, and on the parameter of target value of image quality stored in the storage unit.

2. The image processing apparatus according to claim 1, wherein the storage circuit further stores a parameter of the imaging characteristic of the imaging device, and
   the adjustment control circuit determines the processing parameter when the image processing circuit performs the image processing on the frame image data by using the parameter of the display processing characteristic corresponding to the currently connected display device that is a destination of the frame image data, on the parameter of the target value of image quality, and on the parameter of the imaging characteristic corresponding to the imaging device having transmitted the frame image data to the image processing apparatus.

3. The image processing apparatus according to claim 1, further comprising:
   a user interface circuit allowing users to set the parameter of the target value of image quality,
   wherein the parameter of the target value of the image quality is stored in the storage circuit in connection with an identifier used for identifying users who have set the parameter of the target value of the image quality.

4. The image processing apparatus according to claim 1, wherein the image processing apparatus is able to transmit the parameter of the target value of image quality stored in the storage circuit to another image processing apparatus, or receives the parameter of the target value of image quality from another image processing apparatus.

5. The image processing apparatus according to claim 1, wherein when the image processing apparatus receives the parameter of the target value of image quality from another image processing apparatus, the adjustment control circuit determines the processing parameter which is used when the image processing circuit performs the image processing on the frame image data by using the parameter of the target value of image quality received from another image processing apparatus so that the image quality of images displayed on the display device connected to the image processing apparatus and another display device connected to another image processing apparatus can be equal to each other.

* * * * *